US010309891B2

(12) United States Patent
Muraki et al.

(10) Patent No.: US 10,309,891 B2
(45) Date of Patent: Jun. 4, 2019

(54) PARTICLE SORTING APPARATUS, PARTICLE SORTING METHOD, AND PROGRAM (71) Applicant: Sony Corporation, Tokyo (JP)

(72) Inventors: Yosuke Muraki, Tokyo (JP); Fumitaka Otsuka, Tokyo (JP); Yasunobu Kato, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 15/028,419

(22) PCT Filed: Sep. 10, 2014

(86) PCT No.: PCT/JP2014/074610
§ 371 (c)(1),
(2) Date: Apr. 8, 2016

(87) PCT Pub. No.: WO2015/056516
PCT Pub. Date: Apr. 23, 2015

(65) Prior Publication Data
US 2016/0266027 A1 Sep. 15, 2016

(30) Foreign Application Priority Data
Oct. 16, 2013 (JP) ................................ 2013-215736

(51) Int. Cl.
B03C 7/00 (2006.01)
G01N 15/14 (2006.01)
(Continued)

(52) U.S. Cl.
CPC ........ G01N 15/1404 (2013.01); B01L 3/0268 (2013.01); B01L 3/502776 (2013.01);
(Continued)

(58) Field of Classification Search
CPC .................. B01L 1/04; G01N 15/1404; G01N 2035/00277; G01N 2015/149;
(Continued)

(56) References Cited

U.S. PATENT DOCUMENTS 3,710,933 A 1/1973 Fulwyler et al.
3,826,364 A 7/1974 Bonner et al.
(Continued)

FOREIGN PATENT DOCUMENTS

CN 1950690 A 4/2007
EP 1403633 A2 3/2004
(Continued)

OTHER PUBLICATIONS

Yoshimura et al., The Latest Technology [Modern Technology] of a Cell Sorter, Applied Research Report, Jasco Report. 1990;31(1):1-20.
(Continued)

Primary Examiner — Joseph C Rodriguez
Assistant Examiner — Kalyanavenkateshware Kumar
(74) Attorney, Agent, or Firm — Wolf, Greenfield & Sacks, P.C.

(57) ABSTRACT

[Object] To provide a particle sorting apparatus, a particle sorting method, and a program that are capable of efficiently sorting particles even when sizes of particles to be sorted are not uniform.
[Solving Means] A particle sorting apparatus includes a charge section that imparts charges to at least a part of droplets discharged from an orifice from which a fluid stream is generated, and a charge control section that adjusts a charge amount to be imparted to the droplets by the charge section. Further, the charge control section is structured to adjust the charge amount according to sizes of particles included in the droplets.

9 Claims, 5 Drawing Sheets (51) Int. Cl.
  *B07C 5/342*   (2006.01)
  *B01L 3/02*   (2006.01)
  *B01L 3/00*   (2006.01)
  *B03C 7/06*   (2006.01)
  *G01N 15/00*   (2006.01)
  *G01N 15/10*   (2006.01)

(52) U.S. Cl.
  CPC ......... *B07C 5/342* (2013.01); *G01N 15/1425* (2013.01); *G01N 15/1436* (2013.01); *B01L 3/502723* (2013.01); *B01L 2200/0652* (2013.01); *B01L 2400/0439* (2013.01); *B03C 7/06* (2013.01); *G01N 15/1459* (2013.01); *G01N 15/1484* (2013.01); *G01N 2015/0065* (2013.01); *G01N 2015/1006* (2013.01); *G01N 2015/1081* (2013.01); *G01N 2015/142* (2013.01); *G01N 2015/149* (2013.01)

(58) Field of Classification Search
  CPC .......... G01N 15/02; G01N 15/14; B07C 5/34; B07C 5/342; B03C 7/06
  USPC ................................. 209/3, 127.1, 576, 577
  See application file for complete search history.

(56) References Cited

U.S. PATENT DOCUMENTS

| | | |
|---|---|---|
| 3,924,947 A | 12/1975 | Hogg |
| 4,009,435 A | 2/1977 | Hogg |
| 4,168,460 A | 9/1979 | Menke |
| 4,173,415 A | 11/1979 | Wyatt |
| 4,284,496 A | 8/1981 | Newton |
| 4,318,480 A | 3/1982 | Lombardo et al. |
| 4,318,481 A | 3/1982 | Lombardo et al. |
| 4,325,483 A | 4/1982 | Lombardo et al. |
| 4,538,733 A | 9/1985 | Hoffman |
| 4,616,234 A | 10/1986 | Wint |
| 4,987,539 A | 1/1991 | Moore et al. |
| 5,080,770 A | 1/1992 | Culkin |
| 5,180,065 A | 1/1993 | Touge et al. |
| 5,483,469 A | 1/1996 | Van den Engh et al. |
| 5,602,039 A | 2/1997 | Van den Engh |
| 5,700,692 A | 12/1997 | Sweet |
| 5,776,781 A | 7/1998 | Vardanega et al. |
| 6,079,836 A | 6/2000 | Burr et al. |
| 6,202,734 B1 | 3/2001 | Sackinger et al. |
| 6,248,590 B1 | 6/2001 | Malachowski |
| 6,372,506 B1 | 4/2002 | Norton |
| 6,410,872 B2 | 6/2002 | Campbell et al. |
| 6,589,792 B1 | 7/2003 | Malachowski |
| 6,861,265 B1 | 3/2005 | den Engh |
| 6,941,005 B2 | 9/2005 | Lary et al. |
| 6,949,715 B2 * | 9/2005 | Kelly ....................... B03C 3/08 209/127.1 |
| 7,019,293 B1 | 3/2006 | Hamada |
| 7,024,316 B1 | 4/2006 | Ellison et al. |
| 7,159,752 B2 | 1/2007 | Farnworth |
| 7,417,734 B2 * | 8/2008 | Kanda ................ G01N 15/1459 356/337 |
| 7,639,358 B2 | 12/2009 | Kanda |
| 7,691,636 B2 | 4/2010 | Frazier et al. |
| 7,723,116 B2 | 5/2010 | Evans et al. |
| 7,758,811 B2 | 7/2010 | Durack et al. |
| 7,880,108 B2 | 2/2011 | Schembri et al. |
| 7,901,947 B2 | 3/2011 | Pollack et al. |
| 8,246,805 B2 | 8/2012 | Shinoda |
| 8,570,511 B2 | 10/2013 | Wang |
| 8,681,335 B2 | 3/2014 | Sharpe et al. |
| 8,691,584 B2 | 4/2014 | Durack et al. |
| 8,748,183 B2 | 6/2014 | Durack et al. |
| 8,883,513 B2 | 11/2014 | Pollack et al. |
| 8,922,636 B1 | 12/2014 | Belden et al. |
| 8,922,646 B2 | 12/2014 | Neckels et al. |
| 9,029,724 B2 | 5/2015 | Hashimoto et al. |
| 9,087,371 B2 | 7/2015 | Muraki |
| 9,339,823 B2 | 5/2016 | Muraki et al. |
| 9,429,276 B2 | 8/2016 | Katsumoto |
| 9,588,036 B2 | 3/2017 | Shinoda |
| 9,784,659 B2 | 10/2017 | Tanase et al. |
| 9,784,660 B2 | 10/2017 | Otsuka et al. |
| 9,857,286 B2 | 1/2018 | Muraki et al. |
| 9,958,375 B2 | 5/2018 | Muraki et al. |
| 10,132,735 B2 | 11/2018 | Muraki |
| 2002/0171827 A1 | 11/2002 | van den Engh |
| 2003/0222950 A1 | 12/2003 | Jeanmaire |
| 2004/0062685 A1 | 4/2004 | Norton et al. |
| 2004/0086159 A1 | 5/2004 | Lary et al. |
| 2006/0125856 A1 | 6/2006 | Kitami et al. |
| 2006/0177348 A1 | 8/2006 | Yasuda et al. |
| 2007/0102634 A1 | 5/2007 | Frey et al. |
| 2007/0195310 A1 | 8/2007 | Kanda |
| 2007/0257215 A1 | 11/2007 | Rich |
| 2008/0024619 A1 | 1/2008 | Ono |
| 2008/0050283 A1 | 2/2008 | Chou et al. |
| 2008/0053205 A1 | 3/2008 | Pollack et al. |
| 2008/0067068 A1 | 3/2008 | Li |
| 2008/0092655 A1 | 4/2008 | Takiguchi |
| 2008/0255705 A1 | 10/2008 | Degeal et al. |
| 2008/0284827 A1 | 11/2008 | Fagerquist et al. |
| 2008/0289966 A1 | 11/2008 | Voldman et al. |
| 2009/0125242 A1 | 5/2009 | Choi et al. |
| 2009/0170186 A1 | 7/2009 | Wu et al. |
| 2010/0009445 A1 | 1/2010 | Patra et al. |
| 2010/0118300 A1 | 5/2010 | Wang et al. |
| 2010/0315639 A1 | 12/2010 | Muraki |
| 2011/0005931 A1 | 1/2011 | Zhe et al. |
| 2011/0033339 A1 | 2/2011 | Muraki |
| 2011/0081684 A1 | 4/2011 | Gauer et al. |
| 2011/0221892 A1 | 9/2011 | Neckels et al. |
| 2011/0259749 A1 | 10/2011 | Kanda |
| 2011/0267457 A1 | 11/2011 | Weitz et al. |
| 2011/0275052 A1 | 11/2011 | Schenk et al. |
| 2011/0284378 A1 | 11/2011 | Shinoda |
| 2011/0287976 A1 | 11/2011 | Wang et al. |
| 2012/0076349 A1 | 3/2012 | Manri et al. |
| 2012/0084022 A1 | 4/2012 | Giovangrandi et al. |
| 2012/0135874 A1 | 5/2012 | Wang et al. |
| 2012/0200857 A1 | 8/2012 | Sharpe et al. |
| 2012/0202237 A1 | 8/2012 | Sedoglavich et al. |
| 2012/0247231 A1 | 10/2012 | Kery et al. |
| 2012/0301869 A1 | 11/2012 | Evans |
| 2012/0314096 A1 | 12/2012 | Kruglick |
| 2013/0188040 A1 | 7/2013 | Kamen et al. |
| 2013/0194589 A1 | 8/2013 | Suzuki |
| 2013/0256136 A1 * | 10/2013 | Muraki .................. B03C 7/003 204/555 |
| 2013/0256197 A1 | 10/2013 | Katsumoto |
| 2013/0258075 A1 | 10/2013 | Muraki et al. |
| 2013/0286038 A1 | 10/2013 | Kamath et al. |
| 2014/0021370 A1 | 1/2014 | Suzuki et al. |
| 2014/0043436 A1 | 2/2014 | Bell et al. |
| 2014/0087453 A1 | 3/2014 | Tahara |
| 2014/0097129 A1 | 4/2014 | Foster et al. |
| 2014/0144817 A1 | 5/2014 | Hashimoto et al. |
| 2014/0174206 A1 | 6/2014 | Akiyama et al. |
| 2014/0193059 A1 | 7/2014 | Muraki |
| 2014/0208875 A1 | 7/2014 | Muraki |
| 2014/0212917 A1 | 7/2014 | Durack et al. |
| 2014/0346047 A1 | 11/2014 | Shinoda |
| 2014/0354795 A1 | 12/2014 | Tracy et al. |
| 2015/0057787 A1 | 2/2015 | Muraki et al. |
| 2015/0068957 A1 | 3/2015 | Otsuka et al. |
| 2015/0204774 A1 | 7/2015 | Ito |
| 2015/0285726 A1 | 10/2015 | Tanase et al. |
| 2015/0285727 A1 | 10/2015 | Muraki |
| 2015/0377763 A1 | 12/2015 | Brun et al. |
| 2016/0148433 A1 | 5/2016 | Petrovskaya et al. |
| 2016/0223451 A1 | 8/2016 | Muraki et al. |
| 2016/0245736 A1 | 8/2016 | Muraki et al. |
| 2017/0191925 A1 | 7/2017 | Otsuka et al. |
| 2017/0241889 A1 | 8/2017 | Otsuka et al. |

(56) References Cited

U.S. PATENT DOCUMENTS

| | | | |
|---|---|---|---|
| 2018/0058999 | A1 | 3/2018 | Otsuka et al. |
| 2018/0188150 | A1 | 7/2018 | Muraki et al. |
| 2018/0313740 | A1 | 11/2018 | Otsuka |

FOREIGN PATENT DOCUMENTS

| | | | |
|---|---|---|---|
| GB | 1 103 190 A | 2/1968 | |
| JP | 53-013263 | 2/1978 | |
| JP | 56-030870 A | 3/1981 | |
| JP | 58-187441 U1 | 12/1983 | |
| JP | 62-036542 A | 2/1987 | |
| JP | 62-167478 A | 7/1987 | |
| JP | 64-012245 A | 1/1989 | |
| JP | 09-189653 A | 7/1997 | |
| JP | H09-196855 A | 7/1997 | |
| JP | 10-507525 A | 7/1998 | |
| JP | 11-501258 A | 2/1999 | |
| JP | 2002-505423 A | 2/2002 | |
| JP | 2002-521658 A | 7/2002 | |
| JP | 2004-257756 A | 9/2004 | |
| JP | 2005-315799 A | 11/2005 | |
| JP | 2006-504970 A | 2/2006 | |
| JP | 2006-242849 A | 9/2006 | |
| JP | 2006-292769 A | 10/2006 | |
| JP | 2007-532874 A | 11/2007 | |
| JP | 2008-107110 A | 5/2008 | |
| JP | 2009-145213 A | 7/2009 | |
| JP | 2009-198511 A | 9/2009 | |
| JP | 2009-541093 A | 11/2009 | |
| JP | 2009-298012 A | 12/2009 | |
| JP | 2010-510782 A | 4/2010 | |
| JP | 2010-190680 A | 9/2010 | |
| JP | 2010-216992 A | 9/2010 | |
| JP | 2010-286292 A | 12/2010 | |
| JP | 2010-286341 A | 12/2010 | |
| JP | 2011-033598 A | 2/2011 | |
| JP | 2011-509075 A | 3/2011 | |
| JP | 2011-232033 A | 11/2011 | |
| JP | 2011-237201 A | 11/2011 | |
| JP | 4805417 B1 | 11/2011 | |
| JP | 2012-047464 A | 3/2012 | |
| JP | 2013-210264 A | 10/2013 | |
| JP | 2013-210270 A | 10/2013 | |
| JP | 2015-152439 A | 8/2015 | |
| WO | WO 2001/002836 A1 | 1/2001 | |
| WO | WO 2010/095391 A1 | 8/2010 | |
| WO | WO 2010/129787 A2 | 11/2010 | |
| WO | WO 2010/140460 A1 | 12/2010 | |
| WO | WO 2013/145905 A1 | 10/2013 | |
| WO | WO 2014/115409 A1 | 7/2014 | |

OTHER PUBLICATIONS

Bonner et al., Flourescence Activated Cell Sorting. Review of Scientific Instruments. Mar. 1972; 43(3):404-9.
International Search Report and English translation thereof dated Sep. 27, 2016 in connection with International Application No. PCT/JP2016/070938.
International Search Report and Written Opinion dated Nov. 6, 2015 in connection with International Application No. PCT/JP2015/004282.
International Preliminary Report on Patentability dated Mar. 16, 2017 in connection with International Application No. PCT/JP2015/004282.
International Search Report and Written Opinion and English translation thereof dated Feb. 24, 2015 in connection with International Application No. PCT/JP2014/080588.
Japanese Office Action and English translation thereof dated Dec. 15, 2015 in connection with Japanese Application No. 2012-080366.
Chinese Office Action and English translation thereof dated Mar. 3, 2016 in connection with Chinese Application No. 2013100954250.
International Search Report and Written Opinion dated Mar. 11, 2014 in connection with International Application No. PCT/JP2013/005910.
International Preliminary Report on Patentability dated May 21, 2015 in connection with International Application No. PCT/JP2013/005910.
Japanese Office Action dated Feb. 23, 2016 in connection with Japanese Application No. 2012-246432 and English translation thereof.
International Search Report and English translation thereof dated Mar. 12, 2013 in connection with Application No. PCT/JP2013/053324.
International Preliminary Report on Patentability and English translation thereof dated Oct. 9, 2014 in connection with Application No. PCT/JP2013/053324.
Extended European Search Report dated Aug. 26, 2014 in connection with Application No. 13768656.4.
International Search Report and Written Opinion and English translation thereof dated Mar. 5, 2013 in connection with Application No. PCT/JP2013/052467.
Japanese Office Action dated Jul. 15, 2014 and English translation thereof in connection with Application No. 2013-547043.
International Search Report and Written Opinion and English translation thereof dated Mar. 5, 2013 in connection with Application No. PCT/JP2013/051800.
International Search Report and Written Opinion and English translation thereof dated Jan. 21, 2014 in connection with Application No. PCT/JP2013/081152.
International Preliminary Report on Patentability and English translation thereof dated Oct. 9, 2014 in connection with Application No. PCT/JP2013/051800.
Chinese Office Action dated Aug. 25, 2015 in connection with Chinese Application No. 2013800154978 and English translation thereof.
Extended European Search Report dated Sep. 23, 2016 in connection with European Application No. 13872550.2.
International Preliminary Report on Patentability and English translation thereof dated Aug. 6, 2015 in connection with Application No. PCT/JP2013/081152.
McIntyre et all., Quantitative SLM-based differential interference contrast imaging. Optics Express. Jun. 2010; 18(13):14063-78.
No Author Listed, Differential Interference Contrast, Olympus Microscopy Resource Center, https://web.archive.org/web/20160510073659/http://www.olympusmicro.com:80/primer/techniques/dic/dichome.html, retrieved from the WayBack Machine on Mar. 22, 2018, noting date of May 10, 2016, 2 pages.
No Author Listed, The EPICS® ALTRA™ Flow Cytometer, Sorting Tutorial, Jul. 1, 2000, Coulter International Corporation, 47 pages.
Shapiro, HM, Chapter 6: Flow Sorting, Practical Flow Cytometry, 4th Edition, Dec. 31, 2003, pp. 257-271.
Murphy et al., Differential Interference Contrast, Olympus Microscopy Resource Center, https://web.archive.org/web/20030312041453/http://www.olympusmicro.com:80/primer/techniques/dic/dichome.html, retrieved from the WayBack Machine on Mar. 30, 2018, noting date of Mar. 12, 2003, 3 pages.
U.S. Appl. No. 15/907,805, filed Feb. 28, 2018, Muraki et al.
U.S. Appl. No. 15/506,497, filed Feb. 24, 2017, Otsuka et al.
U.S. Appl. No. 15/116,830, filed Aug. 5, 2016, Otsuka et al.
U.S. Appl. No. 13/788,075, filed Mar. 7, 2013, Muraki et al.
U.S. Appl. No. 13/788,165, filed Mar. 7, 2013, Muraki et al.
U.S. Appl. No. 14/026,023, filed Sep. 13, 2013, Tahara.
U.S. Appl. No. 14/118,788, filed Nov. 19, 2013, Muraki.
U.S. Appl. No. 14/188,994, filed Nov. 20, 2013, Hashimoto et al.
U.S. Appl. No. 14/239,794, filed Feb. 20, 2014, Muraki.
U.S. Appl. No. 14/386,368, filed Sep. 19, 2014, Otsuka et al.
U.S. Appl. No. 14/386,499, filed Sep. 19, 2014, Muraki et al.
U.S. Appl. No. 14/413,543, filed Jan. 8, 2015, Ito.
U.S. Appl. No. 14/440,765, filed May 5, 2015, Tanase et al.
U.S. Appl. No. 14/737,370, filed Jun. 11, 2015, Muraki.
U.S. Appl. No. 14/763,980, filed Jul. 28, 2015, Brun et al.
U.S. Appl. No. 15/028,411, filed Apr. 8, 2016, Muraki et al.
U.S. Appl. No. 15/093,879, filed Apr. 8, 2016, Muraki et al.

(56) References Cited

OTHER PUBLICATIONS

Written Opinion and English translation thereof dated Sep. 27, 2016 in connection with International Application No. PCT/JP2016/070938.

International Preliminary Report on Patentability and English translation thereof dated May 3, 2018 in connection with International Application No. PCT/JP2016/070938.

International Search Report and Written Opinion dated Jan. 8, 2015 in connection with International Application No. PCT/JP2014/005167.

International Preliminary Report on Patentability dated Apr. 28, 2016 in connection with International Application No. PCT/JP2014/005167.

International Search Report and Written Opinion and English translation thereof dated Nov. 18, 2014 in connection with International Application No. PCT/JP2014/074610.

International Preliminary Report on Patentability and English translation thereof dated Apr. 28, 2016 in connection with International Application No. PCT/JP2014/074610.

International Preliminary Report on Patentability and English translation thereof dated Aug. 25, 2016 in connection with International Application No. PCT/JP2014/080588.

Hartman et al., Jet break-up in electrohydrodynamic atomization in the cone-jet mode. J. Aerosol Sci. vol. 31(1), pp. 65-95; Mar. 1999.

Orme et al., Electrostatic charging and deflection of nonconventional droplet streams formed from capillary stream breakup. Phys. Fluids. vol. 12(9); Sep. 2000; pp. 2224-2235.

Yoon et al., 3D particle position and 3D velocity field measurement in microvolume via the defocusing concept. Meas. Sci. Technol. 17 (2006) 2897-2905.

Morton et al., Hydrodynamic metamaterials: Microfabricated arrays to steer, refract, and focus streams of biomaterials. PNAS May 27, 2008. vol. 105(21); 7434-7438.

Luo et al., Three-dimensional tracking of fluorescent particles applied to micro-fluidic measurements. 2006. J. Micromech. Microeng. vol. 16; 1689-1699.

Japanese Office Action dated Feb. 26, 2019 in connection with Japanese Application No. 2015-137487, and English translation thereof.

Pereira et al., Defocusing digital particle image velocimetry and the three-dimensional characterization of two-phase flows. 2002. Meas. Sci. Technol. vol. 13; pp. 683-694.

\* cited by examiner

PARTICLE SORTING APPARATUS, PARTICLE SORTING METHOD, AND PROGRAM

CROSS REFERENCE TO RELATED APPLICATIONS

The present application is a U.S. National Stage Application under 35 U.S.C. § 371, based on International Application No. PCT/JP2014/074610, filed Sep. 10, 2014, which claims priority to Japanese Patent Application JP 2013-215736, filed Oct. 16, 2013, the entire contents of each of which is incorporated herein by reference.

TECHNICAL FIELD

The present technique relates to a particle sorting apparatus, a particle sorting method, and a program, more specifically, to a technique of sorting particles based on an analysis result using an optical method or the like.

BACKGROUND ART

From the past, an optical measurement method that uses flow cytometry (flow cytometer) has been used for analyzing biologically-relevant micro-particles such as cells, microorganisms, and liposomes. A flow cytometer is an apparatus that irradiates light onto micro-particles flowing through a flow channel formed in a flow cell, a microchip, and the like and detects and analyzes fluorescence and scattered light emitted from the individual micro-particles.

Some flow cytometers include a function of sorting and recovering only micro-particles having a specific property based on an analysis result, and a micro-particle apparatus that sorts cells in particular is called "cell sorter". In such a cell sorter, in general, a flow cell or a microchip is vibrated by a vibration device or the like to form droplets of a fluid discharged from the flow channel (see Patent Documents 1 and 2).

After the droplets separated from the fluid is imparted with charges of plus (+) and minus (−), a traveling direction thereof is changed by a deflection plate or the like so that the droplets are recovered in a predetermined vessel or the like. Further, from the past, there has also been proposed a technique of distributing particular cells one by one to each reaction site of a base material used in a PCR (Polymerase Chain Reaction) method or the like using a sorting function of a cell sorter (see Patent Document 3).

Patent Document 1: Japanese Patent Translation Publication No. 2007-532874
Patent Document 2: Japanese Patent Application Laid-open No. 2010-190680
Patent Document 3: Japanese Patent Translation Publication No. 2010-510782

SUMMARY OF INVENTION

Problem to be Solved by the Invention

However, the particle sorting apparatus of the related art described above has a problem that when particles of different sizes coexist in a sample fluid, the traveling direction of droplets becomes unstable so as not to be distributed to a predetermined vessel or reaction site, thus resulting in lowering of sorting accuracy and sorting efficiency.

In this regard, the present disclosure aims at providing a particle sorting apparatus, a particle sorting method, and a program that are capable of efficiently sorting particles even when sizes of particles to be sorted are not uniform.

Means for Solving the Problem

According to the present disclosure, there is provided a particle sorting apparatus including: a charge section that imparts charges to at least a part of droplets discharged from an orifice from which a fluid stream is generated; and a charge control section that adjusts a charge amount to be imparted by the charge section according to sizes of particles included in the droplets.

When the particle sorting apparatus further includes a forward-scattered light detection section that irradiates light onto particles flowing through a flow channel and detects forward-scattered light emitted from the particles by the light irradiation, the charge control section may determine, based on a result of the detection by the forward-scattered light detection section, the charge amount to be imparted to the droplets including the particles.

The charge control section may control the charge section to: impart a first charge amount to the droplets including the particles when an intensity of forward-scattered light detected by the forward-scattered light detection section is smaller than a preset threshold value; and impart a second charge amount different from the first charge amount to the droplets including the particles when the intensity of forward-scattered light detected by the forward-scattered light detection section is equal to or larger than the preset threshold value.

In this case, the second charge amount may be set to be larger than the first charge amount.

The charge control section may change the charge amount to be imparted to the droplets including the particles in proportion to an intensity of forward-scattered light detected by the forward-scattered light detection section.

The charge section may include a charge electrode that is provided while being in contact with a sheath fluid and/or a sample fluid flowing through a flow channel, and the charge control section may change a voltage to be applied to the charge electrode to adjust the charge amount to be imparted to the droplets.

The orifice may be formed in a replaceable microchip. In this case, the charge electrode may be provided in a sheath fluid flow channel provided in the microchip.

The particle sorting apparatus according to the present disclosure may further include: an image pickup device that picks up an image of a state of the droplets; and a droplet judgment section that judges the state of the droplets from the image picked up by the image pickup device, and the charge control section may adjust the charge amount when the droplet judgment section judges that an adjustment is necessary.

The droplet judgment section may judge that the adjustment is necessary when a small droplet not including the particles exists around the droplets including the particles.

According to the present disclosure, there is provided a particle sorting method including the steps of: imparting charges to at least a part of droplets discharged from an orifice from which a fluid stream is generated; and adjusting a charge amount to be imparted to the droplets according to sizes of particles included in the droplets.

According to the present disclosure, there is provided a program that causes a charge control section of a particle sorting apparatus to execute a function of adjusting, according to sizes of particles included in droplets discharged from an orifice from which a fluid stream is generated, a charge amount to be imparted to the droplets.

Effects of the Invention

According to the present disclosure, target particles can be efficiently sorted irrespective of the particle sizes. It should be noted that the effects described herein are not necessarily limited, and any effect described in the present disclosure may be obtained.

MODES FOR CARRYING OUT THE INVENTION

Hereinafter, embodiments of the present disclosure will be described in detail with reference to the attached drawings. It should be noted that the present disclosure is not limited to the following embodiments. Moreover, the descriptions will be given in the following order.

1. First Embodiment
(Example of Sorting Apparatus that Adjusts Charge Amount Based on Particle Size)
2. Second Embodiment
(Example of Sorting Apparatus that Judges Whether to Perform Adjustment Based on Picked-Up Droplet Image)

1. First Embodiment

Figure 1:
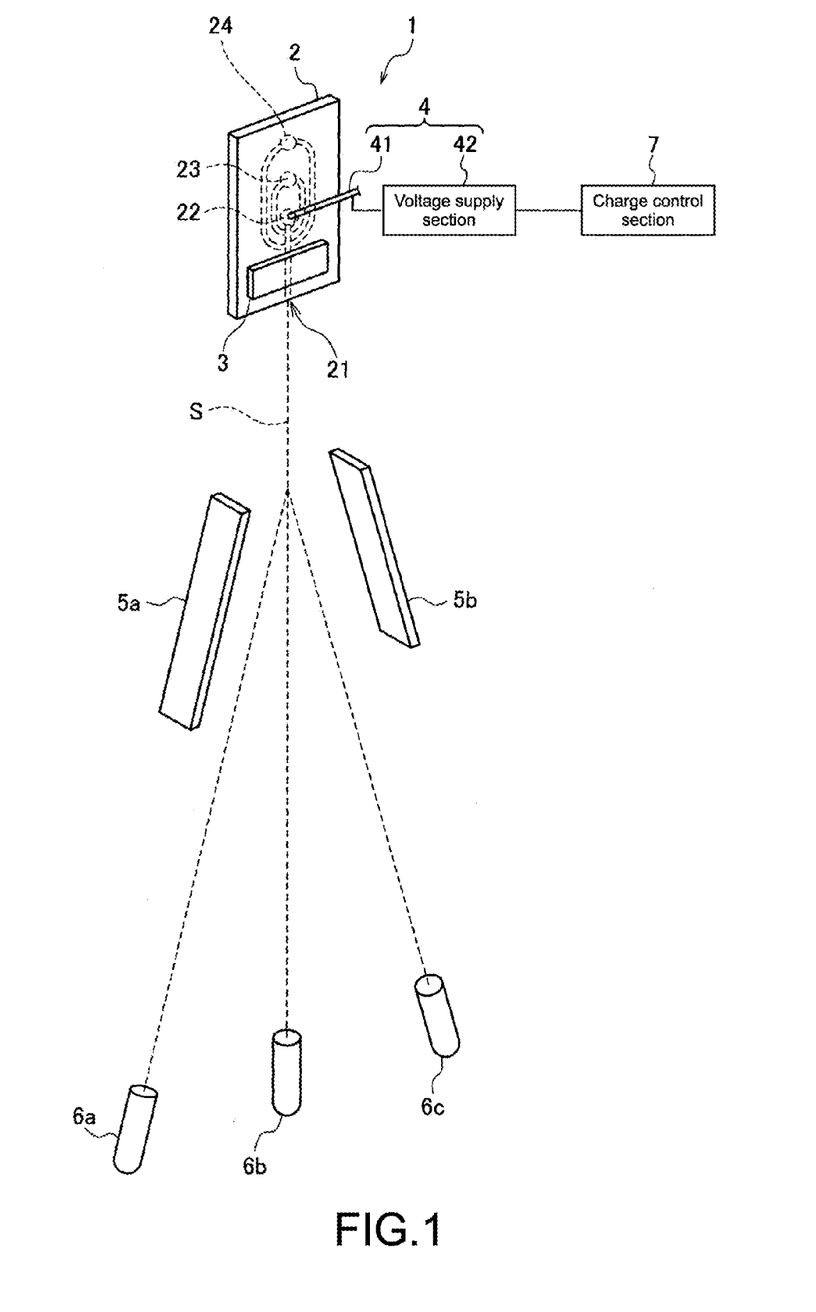
FIG. 1 A diagram schematically showing a structural example of a particle sorting apparatus according to a first embodiment of the present disclosure.

First, a particle sorting apparatus according to a first embodiment of the present disclosure will be described. FIG. 1 is a diagram showing a schematic structure of the particle sorting apparatus according to the first embodiment of the present disclosure.

(Entire Structure of Apparatus)

The particle sorting apparatus 1 of this embodiment sorts and recovers particles based on a result of an analysis using an optical method or the like. As shown in FIG. 1, the particle sorting apparatus 1 includes a microchip 2, a vibration device 3, a charge section 4, a charge control section 7, and deflection plates 5a and 5b.

(Particles)

Particles analyzed and sorted by the particle sorting apparatus 1 of this embodiment widely include biologically-relevant micro-particles such as cells, microorganisms, and liposomes and synthetic particles such as latex particles, gel particles, and industrial particles.

Biologically-relevant micro-particles include chromosomes, liposomes, mitochondria, and organelle (cell organelle) constituting various cells. In addition, cells include plant cells, animal cells, and hemocyte cells. Further, microorganisms include bacteria such as coliform bacillus, viruses such as tobacco mosaic virus, and fungi such as yeast. The biologically-relevant micro-particles may also include biologically-relevant polymer molecules such as nucleic acid, protein, and a complex of those.

On the other hand, industrial particles include particles formed of, for example, an organic polymer material, an inorganic material, and a metal material. As the organic polymer material, polystyrene, styrene divinylbenzene, polymethyl methacrylate, or the like can be used. Moreover, as the inorganic material, glass, silica, a magnetic material, or the like can be used. As the metal material, for example, gold colloid or aluminum can be used. It should be noted that the shape of the particles is generally a sphere, but the shape may be an aspherical shape, and the size, mass, and the like are also not limited in particular.

(Microchip 2)

Formed in the microchip 2 are a sample inlet 22 into which a fluid including particles to be sorted (sample fluid) is introduced, a sheath inlet 23 into which a sheath fluid is introduced, a suction outlet 24 for eliminating clogging and air bubbles, and the like. In the microchip 2, a sample fluid is introduced into the sample inlet 22 to join a sheath fluid introduced into the sheath inlet 23 and is thereafter sent into a sample flow channel to be discharged from an orifice 21 provided at a terminal of the sample flow channel.

Further, a suction flow channel that is in communication with the suction outlet 24 is connected to the sample flow channel. The suction flow channel is used for eliminating, when clogging or air bubble is caused in the sample flow channel, the clogging or air bubble by setting the inside of the sample flow channel to a negative pressure to temporarily cause back-flow. A negative pressure source such as a vacuum pump is connected to the suction outlet 24.

The microchip 2 can be formed of glass and various plastics (PP, PC, COP, PDMS, etc.). The material of the microchip 2 is desirably a material that has permeability with respect to measurement light irradiated from a photodetector to be described later, less auto-fluorescence, and less optical errors due to a small wavelength dispersion.

The microchip 2 can be formed by wet etching or dry etching on a glass substrate or nanoimprint, injection molding, and mechanical processing on a plastic substrate. The microchip 2 can be formed by, for example, sealing a substrate on which a sample flow channel or the like is formed by a substrate formed of the same material or a different material.

(Vibration Device 3)

The vibration device 3 is provided while being in contact with a part of the microchip 2 or as an internal structure of the microchip 2. The vibration device 3 causes the microchip 2 to vibrate at a predetermined frequency and causes minute vibrations with respect to the sheath fluid to form droplets of the fluids (sample fluid and sheath fluid) discharged from the orifice 21, with the result that a fluid stream (flow of droplets) S is generated. As the vibration device 3, a piezo device or the like can be used.

(Charge Section 4)

The charge section 4 imparts positive or negative charges to the droplets discharged from the orifice 21 and is constituted of a charge electrode 41, a voltage source (voltage supply section 42) that applies a predetermined voltage to the charge electrode 41, and the like. The charge electrode 41 is provided while being in contact with the sheath fluid and/or sample fluid flowing through the flow channel and imparts charges to the sheath fluid and/or sample fluid. The charge electrode 41 is inserted into, for example, a charge electrode inlet of the microchip 2.

It should be noted that although the charge electrode 41 is in contact with the sample fluid in FIG. 1, the present disclosure is not limited thereto, and the charge electrode 41 may be provided in contact with the sheath fluid or both the sample fluid and the sheath fluid. It should be noted that considering influences on cells to be sorted, it is desirable to set the charge electrode 41 so that it comes into contact with the sheath fluid.

As described above, by imparting positive or negative charges to desired droplets to charge them, the droplets including arbitrary particles can be separated by an electrical force. Moreover, by synchronizing the charge timing of the charge section 4 and the supply voltage with respect to the vibration device 3, it becomes possible to charge only the arbitrary droplets.

(Deflection Plates 5a and 5b)

The deflection plates 5a and 5b change the traveling direction of the droplets in the fluid stream S by an electrical force that operates among charges imparted to the droplets and induce them to predetermined recovery vessels 6a to 6c, and are provided opposed to each other while sandwiching the fluid stream S. Normally-used electrodes can be used as the deflection plates 5a and 5b, for example.

Different positive or negative voltages are applied to the deflection plates 5a and 5b. As a result, as the charged droplets pass the formed electrical field, an electrical force (coulomb force) is generated, and the droplets are drawn to a direction of either one of the deflection plates 5a and 5b. In the particle sorting apparatus 1, it is possible to control the flow of droplets (side stream) drawn by an electrical field by varying the positive/negative or the charge amount of charges to the droplets, with the result that a plurality of mutually-different particles can be sorted at the same time.

(Recovery Vessels 6a to 6c)

The recovery vessels 6a to 6c recover droplets that have passed between the deflection plates 5a and 5b, and a general-purpose plastic tube, glass tube, and the like can be used for experiments. It is favorable for the recovery vessels 6a to 6c to be provided while being replaceable in the apparatus. In addition, the vessel that recovers non-purpose particles out of the recovery vessels 6a to 6c may be coupled to a drainage channel for recovered droplets.

It should be noted that the number and types of recovery vessels to be provided in the particle sorting apparatus 1 are not limited in particular. For example, when more than 3 recovery vessels are arranged, the droplets only need to be induced to any one of the recovery vessels depending on the presence/absence of the electrical force between the deflection plates 5a and 5b and the magnitude of the force so as to be recovered. Moreover, it is also possible to use a base material in which a plurality of reaction sites (wells) are formed in place of the recovery vessels 6a to 6c and distribute particular particles one by one to the reaction sites.

(Charge Control Section 7)

The charge control section 7 adjusts a charge amount to be imparted by the charge section 4 according to sizes of particles included in the droplets. A method of judging a particle size is not limited in particular. For example, the particle size can be judged based on a result of detecting forward-scattered light measured by the photodetector to be described later. In this case, the charge control section 7 can vary the charge amount to be imparted to the droplets based on whether the intensity of forward-scattered light detected by the photodetector is equal to or larger than a specific value (threshold value) or vary the charge amount to be imparted to the droplets in proportion to the intensity of forward-scattered light.

Furthermore, the charge amount to be imparted to the droplets can be adjusted by controlling the voltage supply section 42 to change the voltage to be applied to the charge electrode 41, for example. In this case, it is favorable for a higher voltage to be applied as the size of particles increases. Accordingly, since charges suited to the particle sizes can be imparted, the droplets can be stably induced by the deflection plates 5a and 5b.

(Photodetector)

Also provided in the particle sorting apparatus 1 of this embodiment is a photodetector (not shown) that irradiates light (measurement light) onto a predetermined site of the sample flow channel and detects light (measurement target light) generated from particles flowing through the sample flow channel, for example. The photodetector can be structured similar to a flow cytometry of the related art. Specifically, the photodetector is constituted of a laser light source, an irradiation system constituted of a collective lens and dichroic mirror that collect and irradiate laser light onto particles, a bandpass filter, and the like, and a detection system that detects measurement target light generated from particles due to laser light irradiation.

The detection system is constituted of, for example, a PMT (Photo Multiplier Tube) and an area image pickup device such as a CCD and a CMOS device. It should be noted that the irradiation system and detection system may also be structured either by the same optical path or different optical paths. Moreover, the measurement target light detected by the detection system of the photodetector is light generated from particles due to irradiation of measurement light and may be, for example, forward-scattered light or side-scattered light, various types of scattered light caused by Rayleigh scattering and Mie scattering, fluorescence, and the like.

Of those measurement target light, forward-scattered light becomes an index for evaluating the particle size since its intensity varies in proportion to a surface area of cells. Therefore, it is favorable for the particle sorting apparatus 1 of this embodiment to include a forward-scattered light detection section that detects forward-scattered light so that the charge amount adjustment by the charge control section 7 can be performed with ease.

(Operations)

Figure 2:
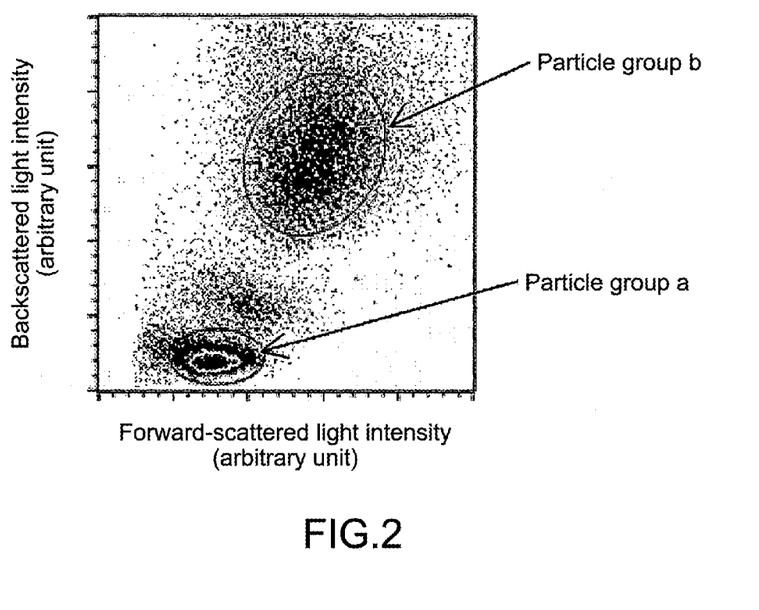
FIG. 2 A figure substitution graph showing a detection result of particles in a photodetector, the abscissa axis representing an intensity of forward-scattered light and the ordinate axis representing an intensity of backscattered light.

Next, operations of the particle sorting apparatus 1 of this embodiment, that is, a method of sorting particles using the particle sorting apparatus 1 will be described while taking a case where a charge amount is adjusted based on a detection result of forward-scattered light as an example. FIG. 2 shows a detection result of particles in the photodetector, the abscissa axis representing an intensity of forward-scattered light and the ordinate axis representing an intensity of backscattered light.

When sorting particles by the particle sorting apparatus 1 of this embodiment, the sample fluid including particles to be sorted is introduced into the sample inlet 22, and the sheath fluid is introduced into the sheath inlet 23. Then, for example, the photodetector detects a particle flow speed (flow rate) and particle intervals simultaneous with a detection of optical properties of particles. The detected optical properties of particles, flow rate, intervals, and the like are converted into electrical signals and output to an overall control section (not shown) of the apparatus.

The laminar flow of the sample fluid and sheath fluid that has passed a light irradiation section of the sample flow channel is discharged to a space outside the microchip 2 from the orifice 21. At this time, the orifice 21 is vibrated by the vibration device 3 so that the fluid to be discharged is formed into droplets. Then, the traveling direction of charged droplets in the sample flow channel is changed by the deflection plates 5a and 5b to be induced to and recovered in the predetermined recovery vessels 6a to 6c based on the detection result obtained by the photodetector.

Figure 3:
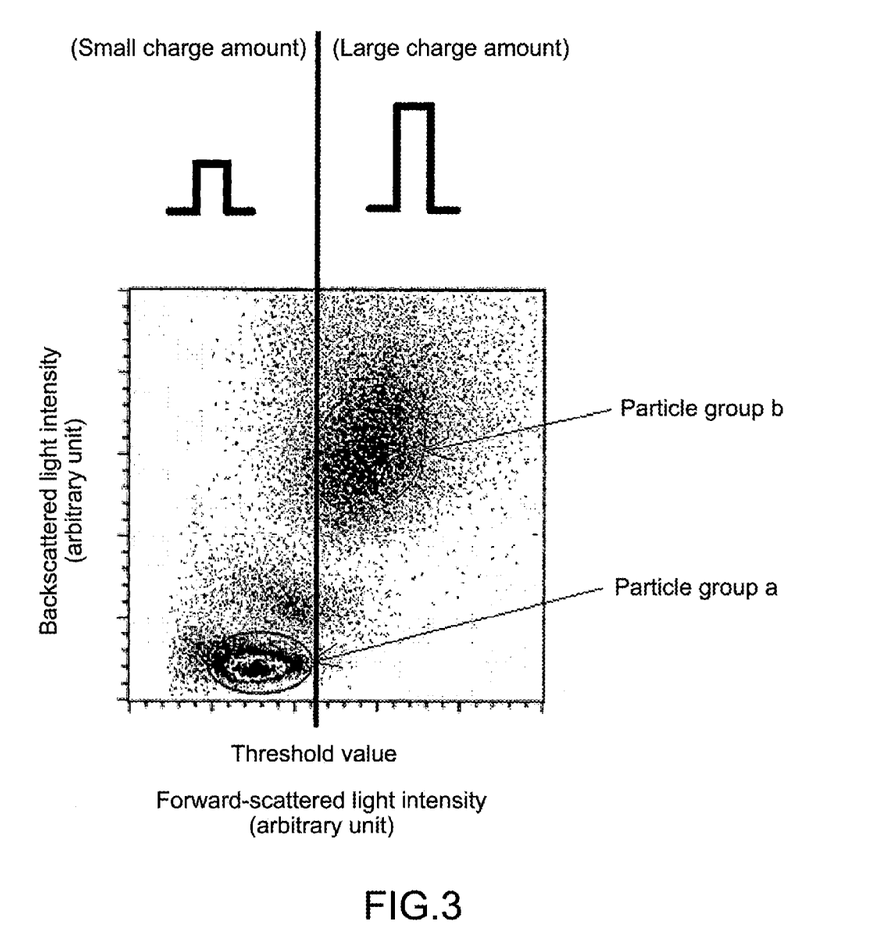
FIG. 3 A figure substitution graph showing an example of a charge amount adjustment method by a charge control section 7.

At this time, in the particle sorting apparatus 1 of this embodiment, the charge amount to be imparted by the charge section 4 is adjusted according to sizes of particles included in the droplets. FIG. 3 is a diagram showing an example of the charge amount adjustment method by the charge control section 7. For example, the sample fluid includes particles of the same type or different types and of different sizes, and when the detection result as shown in FIG. 2 is obtained by the photodetector, the charge control section 7 can determine the charge amount to be imparted to the droplets including the particles based on forward-scattered light.

Here, the particle group a shown in FIG. 2 is a particle whose particle size is relatively small, and the particle group b is a particle whose particle size is relatively large. When adjusting the charge amount to be imparted to the droplets including those particles in two steps, a threshold value is preset for the intensity of forward-scattered light as shown in FIG. 3. Then, the charge control section 7 determines a charge amount to be imparted to the droplets including the particles whose intensity of forward-scattered light is equal to or larger than the threshold value (particle group b) (second charge amount) and a charge amount to be imparted to the droplets including the particles whose intensity of forward-scattered light is smaller than the threshold value (particle group a) (first charge amount).

Specifically, the charge control section 7 controls the voltage supply section 42 so that the second charge amount becomes larger than the first charge amount, that is, a higher voltage is applied to the droplets including the particles of the particle group b than the droplets including the particles of the particle group a. The charge amount adjustment based on forward-scattered light is not limited to the two-step adjustment, and by setting a plurality of threshold values, the adjustment can be performed while categorizing particles in 3 or more steps. The threshold values can be set arbitrarily by a user, so the adjustment can be performed as appropriate according to cells to be sorted.

Further, the charge amount to be imparted to the droplets including the particles can be changed in proportion to the intensity of forward-scattered light detected by the photodetector without setting a threshold value. In this case, the charge control section 7 controls the voltage supply section 42 so that a higher voltage is applied to droplets including particles having a higher intensity of forward-scattered light.

It is possible to cause the charge control section 7 to perform the charge amount adjustment described above by creating a program for realizing a function of adjusting a charge amount to be imparted to droplets according to sizes of particles included in the droplets and mounting the program in the charge control section 7 of the particle sorting apparatus 1.

It should be noted that although the first embodiment above exemplifies the case of using the microchip 2, the present disclosure is not limited thereto, and the same effect can be obtained even when a flow cell is used in place of the microchip 2.

As described above in detail, since the charge amount to be imparted by the charge section is adjusted according to sizes of particles included in the droplets in the particle sorting apparatus of this embodiment, the traveling direction of the droplets can be stabilized irrespective of the particle sizes. As a result, the particles can be efficiently sorted even when the sizes of particles to be sorted, that are included in the sample fluid, are not uniform.

2. Second Embodiment

Figure 4:
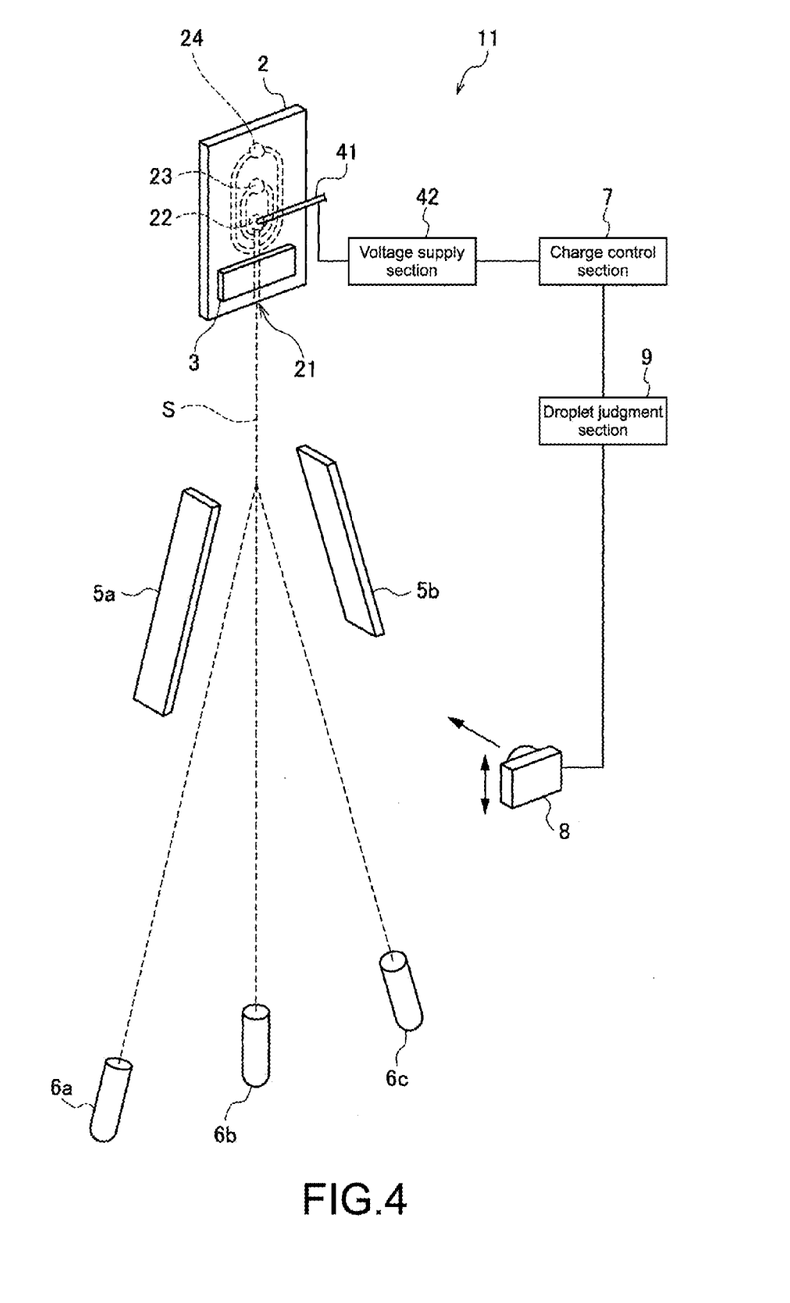
FIG. 4 A diagram schematically showing a structural example of a particle sorting apparatus according to a second embodiment of the present disclosure.

Next, a particle sorting apparatus according to a second embodiment of the present disclosure will be described. FIG. 4 is a diagram schematically showing a structural example of the particle sorting apparatus according to the second embodiment of the present disclosure. As shown in FIG. 4, the particle sorting apparatus 11 of this embodiment includes an image pickup device (camera) 8 that picks up an image of a droplet state and a droplet judgment section 9 that judges the droplet state in addition to the structure of the first embodiment described above.

(Image Pickup Device (Camera) 8)

The image pickup device (camera) 8 picks up an image of a state of droplets that have passed the deflection plates 5a and 5b. It should be noted that for the image pickup of droplets, various image pickup devices such as a photoelectric conversion device can be used in addition to image pickup apparatuses such as a CCD and a CMOS camera. Moreover, a movement mechanism for changing a position can be provided in the camera 8. In addition, a light source (not shown) that illuminates a photograph area may be provided with the camera 8 in the particle sorting apparatus 11 of this embodiment.

(Droplet Judgment Section 9)

The droplet judgment section 9 judges a state of droplets based on an image picked up by the camera 8 and outputs the result to the charge control section 7. The droplet judgment section 9 judges that an adjustment is necessary when there is a small droplet not including a particle (side strip) around the droplet including a particle, for example.

(Droplet Judgment Step)

Figure 5:
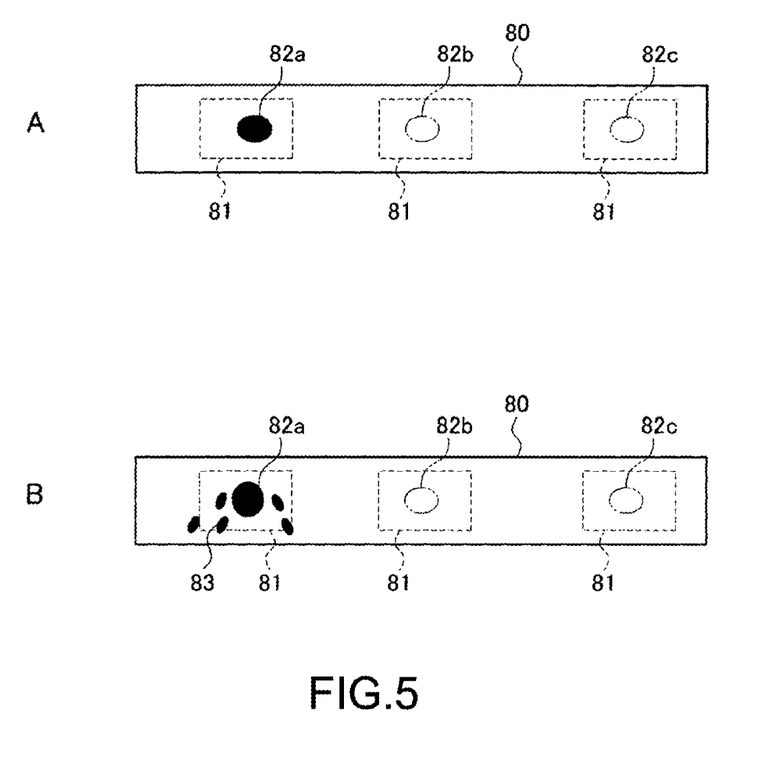
FIGS. 5A and 5B are diagrams each showing an image taken by a camera 8.

First, charged droplets are photographed by the camera 8. FIGS. 5A and 5B are diagrams each showing an example of an image taken by the camera 8. In the image 80 in a case where the charge amount is appropriate, side strips 83 are not generated around a droplet 82a as shown in FIG. 5A. In contrast, in the image 80 in a case where the charge amount is inappropriate, the side strips 83 are generated around the droplet 82a as shown in FIG. 5B.

In this regard, in the particle sorting apparatus 11 of this embodiment, states of the droplets 82a to 82c are photographed by the camera 8, and whether the side strips 83 are generated is checked by the droplet judgment section 9. The method of checking the side strips 83 by the droplet judgment section 9 is not limited in particular. For example, whether the side strips 83 are generated can be checked by setting a judgment area 81 including the droplet 82a and carrying out image recognition processing on the judgment area 81.

As a result, when confirmed that the side strip 83 exists, the droplet judgment section 9 judges that the charge amount needs to be adjusted and outputs the judgment result to the charge control section 7. Accordingly, the charge control section 7 adjusts the charge amount. For example, when the side strip 83 is more on the outside than the expected position, the charge amount is reduced by judging that the charge is too strong and in an opposite case, increases the charge amount by judging that the charge is too weak.

Since the particle sorting apparatus 11 of this embodiment judges the droplet state based on the image 80 taken by the camera 8 to judge whether the charge amount is to be adjusted, an adjustment that matches an actual condition can be performed.

It should be noted that the structures and effects of the particle sorting apparatus of this embodiment other than those described above are the same as those of the first embodiment described above.

Furthermore, the present disclosure may also take the following structures.

(1) A particle sorting apparatus, including:
a charge section that imparts charges to at least a part of droplets discharged from an orifice from which a fluid stream is generated; and
a charge control section that adjusts a charge amount to be imparted by the charge section according to sizes of particles included in the droplets.

(2) The particle sorting apparatus according to (1), further including
a forward-scattered light detection section that irradiates light onto particles flowing through a flow channel and detects forward-scattered light emitted from the particles by the light irradiation,
in which the charge control section determines, based on a result of the detection by the forward-scattered light detection section, the charge amount to be imparted to the droplets including the particles.

(3) The particle sorting apparatus according to (2),
in which the charge control section controls the charge section to:
impart a first charge amount to the droplets including the particles when an intensity of forward-scattered light detected by the forward-scattered light detection section is smaller than a preset threshold value; and
impart a second charge amount different from the first charge amount to the droplets including the particles when the intensity of forward-scattered light detected by the forward-scattered light detection section is equal to or larger than the preset threshold value.

(4) The particle sorting apparatus according to (3),
in which the second charge amount is larger than the first charge amount.

(5) The particle sorting apparatus according to any one of (2) to (4),
in which the charge control section changes the charge amount to be imparted to the droplets including the particles in proportion to an intensity of forward-scattered light detected by the forward-scattered light detection section.

(6) The particle sorting apparatus according to any one of (1) to (5), in which:
the charge section includes a charge electrode that is provided while being in contact with a sheath fluid and/or a sample fluid flowing through a flow channel; and
the charge control section changes a voltage to be applied to the charge electrode to adjust the charge amount to be imparted to the droplets.

(7) The particle sorting apparatus according to (6),
in which the orifice is formed in a replaceable microchip, and the charge electrode is provided in a sheath fluid flow channel provided in the microchip.

(8) The particle sorting apparatus according to any one of (1) to (7), further including:
an image pickup device that picks up an image of a state of the droplets; and
a droplet judgment section that judges the state of the droplets from the image picked up by the image pickup device,
in which the charge control section adjusts the charge amount when the droplet judgment section judges that an adjustment is necessary.

(9) The particle sorting apparatus according to (8),
in which the droplet judgment section judges that the adjustment is necessary when a small droplet not including the particles exists around the droplets including the particles.

(10) A particle sorting method, including the steps of:
imparting charges to at least a part of droplets discharged from an orifice from which a fluid stream is generated; and
adjusting a charge amount to be imparted to the droplets according to sizes of particles included in the droplets.

(11) A program that causes a charge control section of a particle sorting apparatus to execute
a function of adjusting, according to sizes of particles included in droplets discharged from an orifice from which a fluid stream is generated, a charge amount to be imparted to the droplets.

DESCRIPTION OF SYMBOLS 1, 11 particle sorting apparatus
2 microchip
3 vibration device
4 charge section
5a, 5b deflection plate
6a-6c recovery vessel
7 charge control section
8 image pickup device (camera)
9 droplet judgment section
21 orifice
22 sample inlet
23 sheath inlet
24 suction outlet
41 charge electrode
42 voltage supply section
80 image
81 judgment area
82a-82c droplet
83 side strip
S fluid stream

The invention claimed is:

1. A particle sorting apparatus, comprising:
a charge section that imparts charges to at least a part of droplets discharged from an orifice from which a fluid stream is generated; and
a charge control section that adjusts a charge amount to be imparted by the charge section according to sizes of particles included in the droplets based on a result of scattered light emitted from the particles by irradiating light onto particles;
an image pickup device that picks up an image of a state of the droplets; and
a droplet judgment section that judges the state of the droplets from the image picked up by the image pickup device,
wherein the charge control section adjusts the charge amount when the droplet judgment section judges that an adjustment is necessary;
wherein the droplet judgment section judges that the adjustment is necessary when a small droplet not including the particles exists around the droplets including the particles;

wherein the sizes of the particles in the droplets are not uniform.

2. The particle sorting apparatus according to claim 1, further comprising
a forward-scattered light detection section that irradiates light onto particles flowing through a flow channel and detects forward-scattered light emitted from the particles by the light irradiation,
wherein the charge control section determines, based on a result of the detection by the forward-scattered light detection section, the charge amount to be imparted to the droplets including the particles.

3. The particle sorting apparatus according to claim 2,
wherein the charge control section controls the charge section to:
impart a first charge amount to the droplets including the particles when an intensity of forward-scattered light detected by the forward-scattered light detection section is smaller than a preset threshold value; and
impart a second charge amount different from the first charge amount to the droplets including the particles when the intensity of forward-scattered light detected by the forward-scattered light detection section is equal to or larger than the preset threshold value.

4. The particle sorting apparatus according to claim 3,
wherein the second charge amount is larger than the first charge amount.

5. The particle sorting apparatus according to claim 2,
wherein the charge control section changes the charge amount to be imparted to the droplets including the particles in proportion to an intensity of forward-scattered light detected by the forward-scattered light detection section.

6. The particle sorting apparatus according to claim 1, wherein:
the charge section includes a charge electrode that is provided while being in contact with a sheath fluid and/or a sample fluid flowing through a flow channel; and
the charge control section changes a voltage to be applied to the charge electrode to adjust the charge amount to be imparted to the droplets.

7. The particle sorting apparatus according to claim 6,
wherein the orifice is formed in a replaceable microchip, and the charge electrode is provided in a sheath fluid flow channel provided in the microchip.

8. A particle sorting method, comprising the steps of:
imparting charges to at least a part of droplets discharged from an orifice from which a fluid stream is generated; and
adjusting a charge amount to be imparted to the droplets according to sizes of particles included in the droplets based on a result of scattered light emitted from the particles by irradiating light onto particles;
an image pickup device that picks up an image of a state of the droplets; and
a droplet judgment section that judges the state of the droplets from the image picked up by the image pickup device,
wherein the charge control section adjusts the charge amount when the droplet judgment section judges that an adjustment is necessary;
wherein the droplet judgment section judges that the adjustment is necessary when a small droplet not including the particles exists around the droplets including the particles;
wherein the sizes of the particles in the droplets are not uniform.

9. A non-transitory computer readable storage medium having computer readable instructions stored thereon that, when executed, cause a charge control section of a particle sorting apparatus to execute
a function of adjusting, according to sizes of particles included in droplets discharged from an orifice from which a fluid stream is generated, a charge amount to be imparted to the droplets based on a result of scattered light emitted from the particles by irradiating light onto particles;
an image pickup device that picks up an image of a state of the droplets; and
a droplet judgment section that judges the state of the droplets from the image picked up by the image pickup device,
wherein the charge control section adjusts the charge amount when the droplet judgment section judges that an adjustment is necessary;
wherein the droplet judgment section judges that the adjustment is necessary when a small droplet not including the particles exists around the droplets including the particles;
wherein the sizes of the particles in the droplets are not uniform.

* * * * *